United States Patent
Mark

[19]

[11] Patent Number: 6,070,477
[45] Date of Patent: Jun. 6, 2000

[54] COLLAPSIBLE SHEATH FLUID RESERVOIRS FOR FLOW CYTOMETERS

[75] Inventor: Graham A. Mark, Los Alamos, N. Mex.

[73] Assignees: The Regents of the University of California; Los Alamos National Laboratory, both of Los Alamos, N. Mex.

[21] Appl. No.: 09/118,983

[22] Filed: Jul. 17, 1998

Related U.S. Application Data

[60] Provisional application No. 60/053,038, Jul. 18, 1997.

[51] Int. Cl.[7] .................................................. G01N 1/00
[52] U.S. Cl. ................................................. 73/865.5
[58] Field of Search ..................... 73/865.5, 863; 324/71.4; 220/501, 529, 530; 383/37, 38, 42; 356/438, 440, 441, 442; 250/343

[56] References Cited

U.S. PATENT DOCUMENTS

| | | |
|---|---|---|
| 2,758,747 | 8/1956 | Stevens . |
| 4,673,288 | 6/1987 | Thomas et al. ............................ 356/72 |
| 4,844,610 | 7/1989 | North, Jr. .................................. 356/73 |
| 5,270,548 | 12/1993 | Steinkamp ........................... 250/461.2 |
| 5,395,588 | 3/1995 | North, Jr. et al. ........................ 422/81 |

FOREIGN PATENT DOCUMENTS

| | | |
|---|---|---|
| 93197A | 11/1983 | European Pat. Off. . |

*Primary Examiner*—Robert Raevis
*Attorney, Agent, or Firm*—DeWitt M. Morgan; William A. Eklund; Gamma Morrison Bennett

[57] ABSTRACT

The present invention is a container in the form of a single housing for holding fluid, including a first collapsible reservoir having a first valve. The first reservoir initially contains a volume of fluid. The container also includes a second reservoir, initially empty (or substantially empty), expandable to a second volume. The second reservoir has a second valve. As the volume of said first reservoir decreases, the volume of the second reservoir proportionally increases.

12 Claims, 6 Drawing Sheets

COLLAPSIBLE SHEATH FLUID RESERVOIRS FOR FLOW CYTOMETERS

This application claims priority to U.S. Provisional Patent Application Ser. No. 60/053,038, filed Jul. 18, 1997.

GOVERNMENT RIGHTS CLAUSE

This invention is made with U.S. Government support under Contract No. W-7405-ENG-36 awarded by the U.S. Department of Energy. Accordingly, the U.S. Government has certain rights in this invention.

FIELD OF THE INVENTION

The present invention relates to sheath fluid reservoirs for flow cytometers and, in particular, to apparatus for minimizing the volume of sheath fluid reservoirs.

BACKGROUND OF THE INVENTION

Flow cytometry is an important analytical tool for detecting characteristic fluorescence emission intensities from cellular components such as DNA, RNA, proteins, enzymes, and lipids. The components are stained with fluorescent dyes, antigenic determinants labeled with antibodies conjugated to fluorochrome, hybridized to DNA sequences labeled with fluorescent probes, or labeled with some other type of fluorescent labeling technique. The resulting emission intensity is measured at high speed on a cell-by-cell basis. Fluorescence signal intensity, signal width and area are among the fluorescence emission characteristics measured by the cytometer. The device works by measuring the desired characteristic at specified wavelength regions within the fluorescence spectra when the stained cells or particles intersect a cw laser or arc lamp excitation source. Conventional flow cytometry has become an important clinical diagnostic and biomedical research tool, demanding ever-expanding capabilities to meet clinical and research needs.

To be studied, the labeled biological material is added to a liquid which is termed "sheath fluid." The sheath fluid and biological material mixture is passed through the fluidic passages of the flow cytometer, where the desired measurements are made. The apparatus for handling the sheath fluid includes a reservoir for unused or clean sheath fluid and a reservoir for waste sheath fluid which has passed through the fluidic passages of the flow cytometer. Fluid is pumped from the clean fluid reservoir through the fluidic passages to the waste fluid reservoir. The problem with existing sheath fluid reservoirs is the space they occupy; essentially twice the volume of the sheath fluid being used.

Accordingly, it is the object of the present invention to reduce the combined volumes of the two sheath fluid containers by, essentially, 50%.

It is another object of the invention to consolidate the two sheath fluid containers into a single container, preferably a disposable container.

It is a further object of the invention to minimize the combined volumes of the two sheath fluid containers by the use of collapsible and expandable reservoirs in the same container; wherein as the clean fluid reservoir collapses, the waste reservoir expands. Thus, the same physical space (or volume) is used to store both clean and waste sheath fluid, thereby halving the volume utilized by prior art sheath fluid containers.

It is a further object of the invention to simplify the packaging and handling of sheath fluid, with two reservoirs packaged in a single disposable container (e.g., a cardboard box).

Flexible containers for liquids which collapse as liquid is removed from the container are known. However, no applications of flexible containers for flow cytometry are known. Furthermore, there are numerous patents drawn to the flow cytometry art, such as U.S. Pat. No. 5,270,540 which discloses a "phase-sensitive" flow cytometer, allowing the use of multiple fluorochromes during one measuring cycle. No patents in this area were found which suggest any alterations to the standard sheath fluid reservoir system.

SUMMARY OF THE INVENTION

The present invention comprises a container, in the form of a single housing, for holding both clean and waste sheath fluid for use in a flow cytometer. The container includes a first sealed collapsible reservoir, having a first valve, where this first reservoir holds a volume of clean sheath fluid. The container also includes a second sealed reservoir, expandable to a second volume, having a second valve. In operation, the volume of the first reservoir decreases as the clean sheath fluid is used and the volume of the second reservoir expands with deposit of the waste sheath fluid. Preferably, the reservoirs are made of flexible waterproof material, such as aluminum coated Mylar™ (Dupont, Wilmington, Del.). Also preferably, the housing is disposable, being made of cardboard or similar material. The second reservoir typically contains a volume of disinfectant sufficient to sterilize the waste sheath fluid. This constant volume reservoir system can be utilized in flow cytometers using pump delivery mode, pressurized sheath delivery, or vacuum driven flow.

DESCRIPTION OF THE PREFERRED EMBODIMENT

Figure 1:
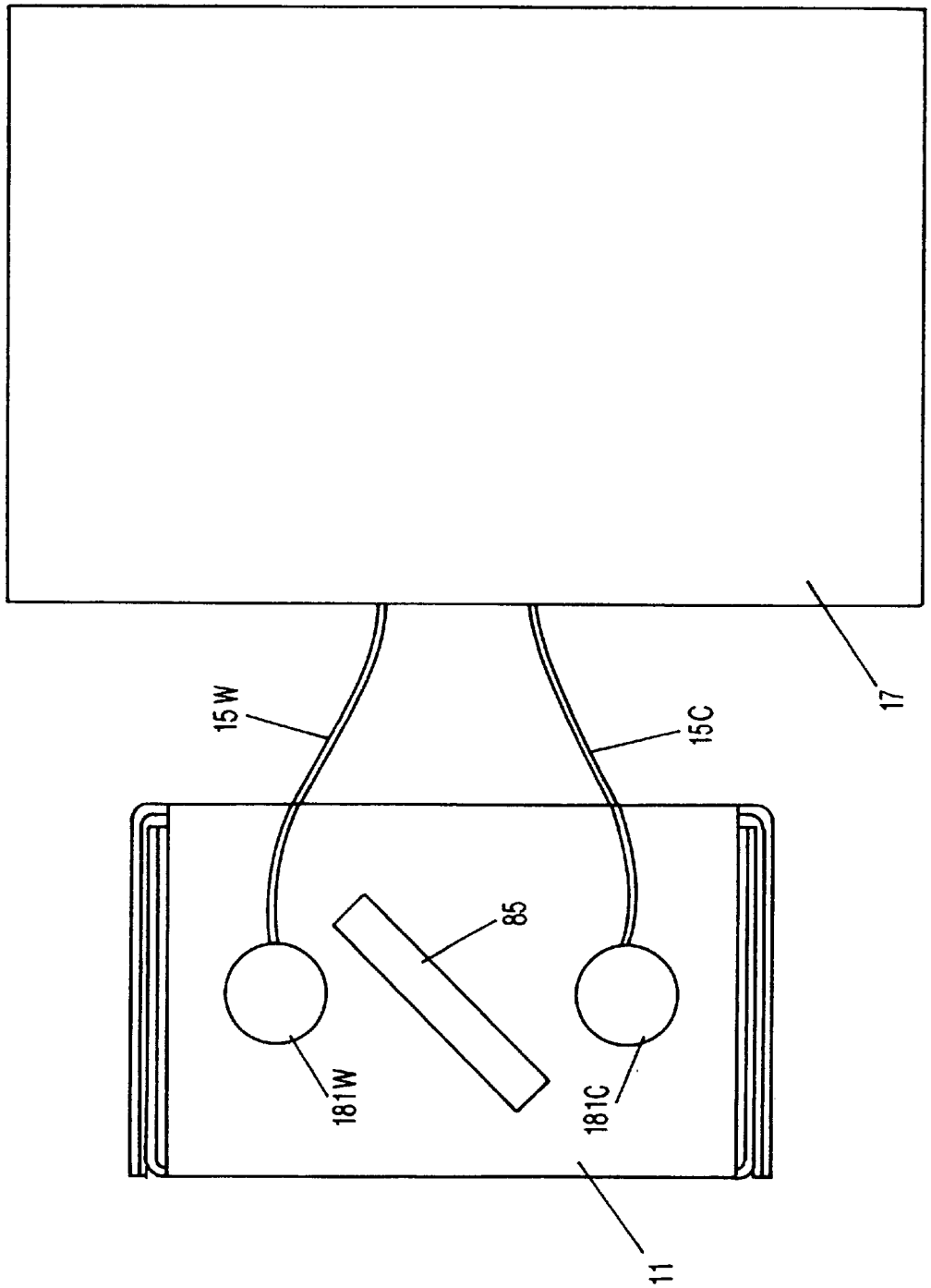
FIG. 1 is a front view of the fully assembled sheath fluid container of the present invention connected with a schematically illustrated flow cytometer.
Figure 2:
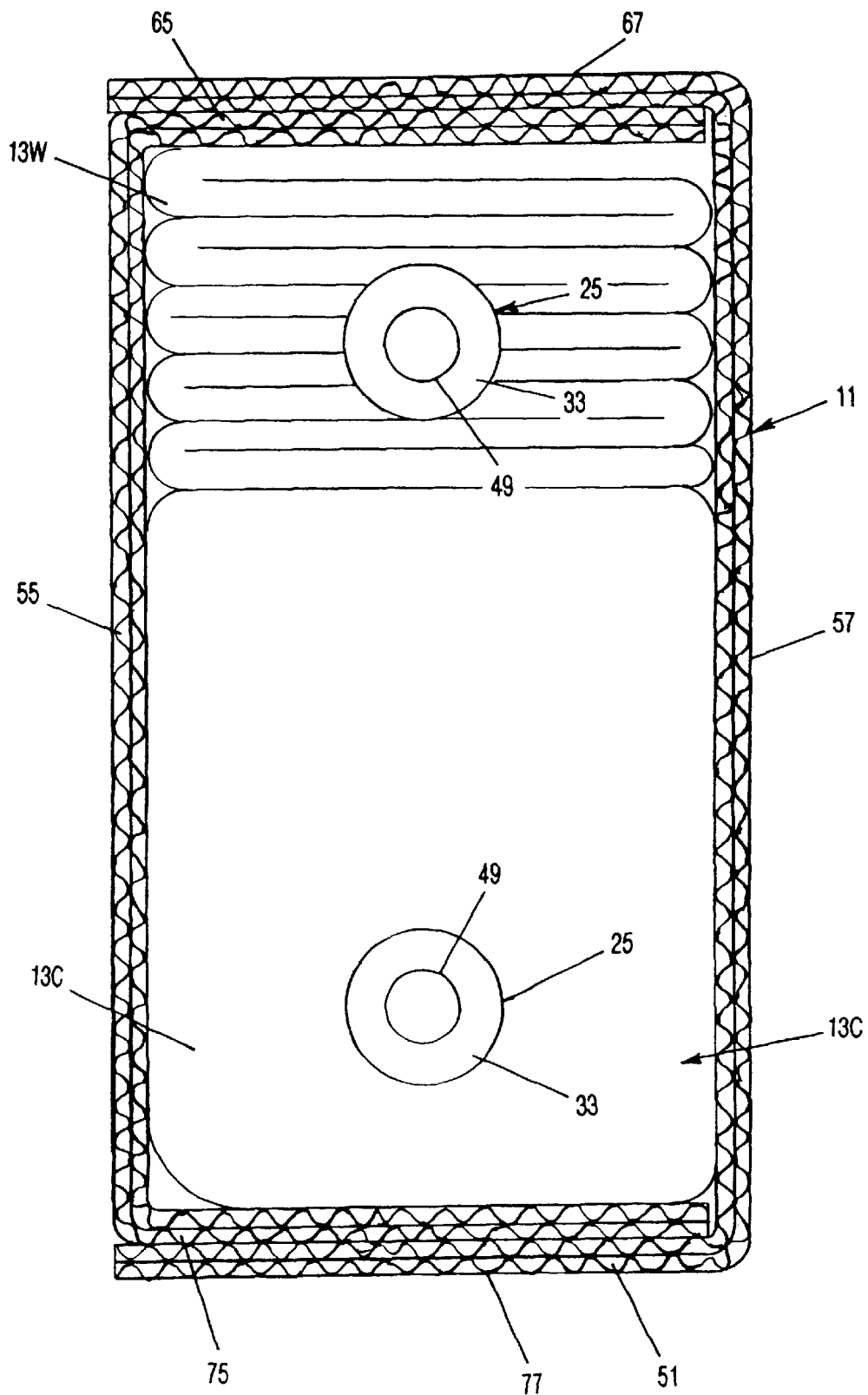
FIG. 2 is a front end view of the sheath fluid container of the present invention in its assembled form, but with the front end panel broken away to show the relative positions of the two collapsible/expandable sheath fluid reservoirs of the present invention (one essentially empty; the other, full)

With reference to FIGS. 1 and 2, the preferred embodiment of the present invention includes a sheath fluid container 11, two collapsible/expandable sheath fluid reservoirs 13C and 13W ("C" for clean and "W" for waste), and tubing 15C and 15W to connect reservoirs 13C and 13W to flow cytometer 17. Flow cytometer 17 is of any known design, and can include a pump (not shown) and tubing (also not shown) through which the sheath fluid passes as the biological material carried by the sheath fluid are analyzed. As the method of moving the sheath fluid and the biological material mixture, such as a pump or vacuum, forms no part of the present invention, it is not described herein. However, basic information about flow cytometry can be found in U.S. Pat. No. 4,673,288, issued to Thomas et al., a pressurized system is described in U.S. Pat. No. 4,844,610 and a vacuum based flow cytometer control system is described in U.S. Pat. No. 5,395,588, both issued to North, Jr. et al.

Figure 3:
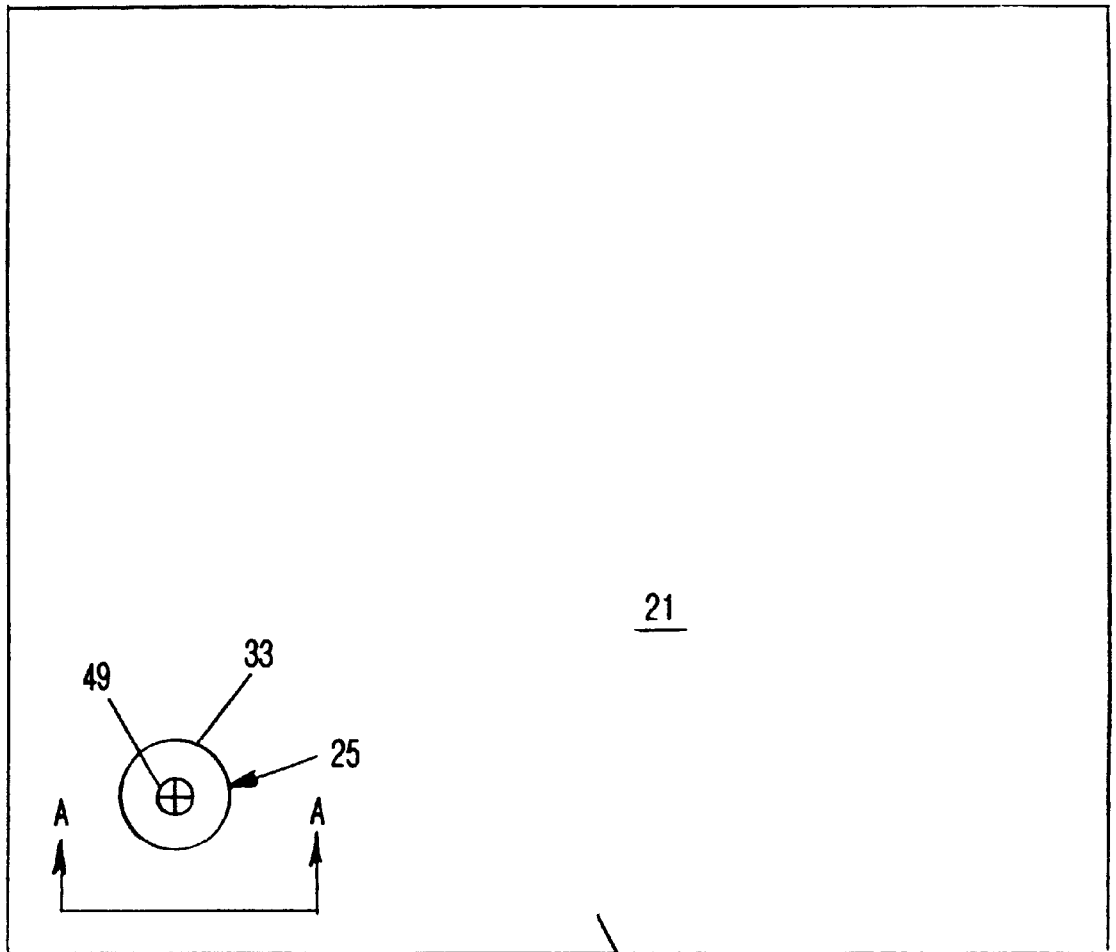
FIG. 3 is a plain view of one of the two typically identical collapsible/expandable sheath fluid reservoirs of the present invention, in its empty/essentially empty and flattened condition.
Figure 4:
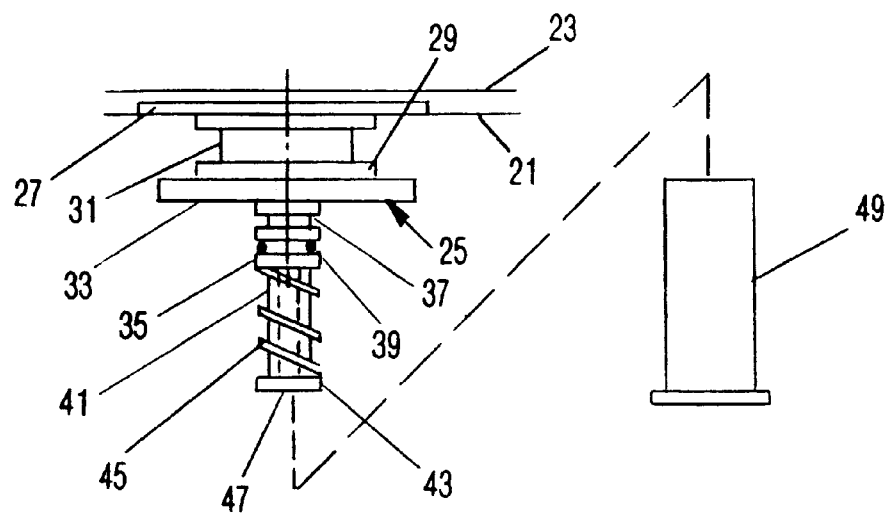
FIG. 4 is a side view, taken along lines A—A of FIG. 3, of a preferred valve mechanism to be incorporated in the sheath fluid reservoirs.

Collapsible/expandable sheath fluid reservoirs 13C and 13W are preferably Mylar™ type bags, similar to the type used in wine boxes. With reference to FIGS. 3 and 4, reservoir 13C (shown in its flattened condition) includes first and second rectangular shaped panels 21 and 23, and a valve assembly 25. Reservoirs 13C and 13W, with valve assemblies 25, are of the type supplied by David S. Smith Liquid Packaging Co., Rugby, England. Panels 21 and 23 are of aluminum coated Mylar, which are bonded to each other adjacent to the edges thereof by any conventional technique. Valve assembly 25 is, preferably, formed of inert plastic and includes a first washer shaped element 27 which is positioned on the inside of panel 21, as illustrated in FIG. 4, and bonded (in any conventional manner) to panel 21 to form a hermetic seal therewith. Valve assembly 25 also includes a spacer element 29, having a circumferentially extending groove 31 therein, a second washer shaped element 33, and a nipple portion 35, having two circumferentially extending grooves 37. An O-ring 39 is received in, at least, one of grooves 37. The valve assembly 25 also includes a plunger 41 having a spring retaining lip 43, compression spring 45, and through passage 47. Spring 45 is captured between lip 43 and nipple portion 35, to bias plunger in its extended and closed position. As the valve assembly is of conventional design, the internal parts are not illustrated. Finally, valve assembly 25 includes a cap 49 which fits over plunger 41, with the interior, cylindrical surface thereof sealing with O-ring 39. Preferably, sheath fluid reservoir 13W is identical to reservoir 13C.

Figure 5A:
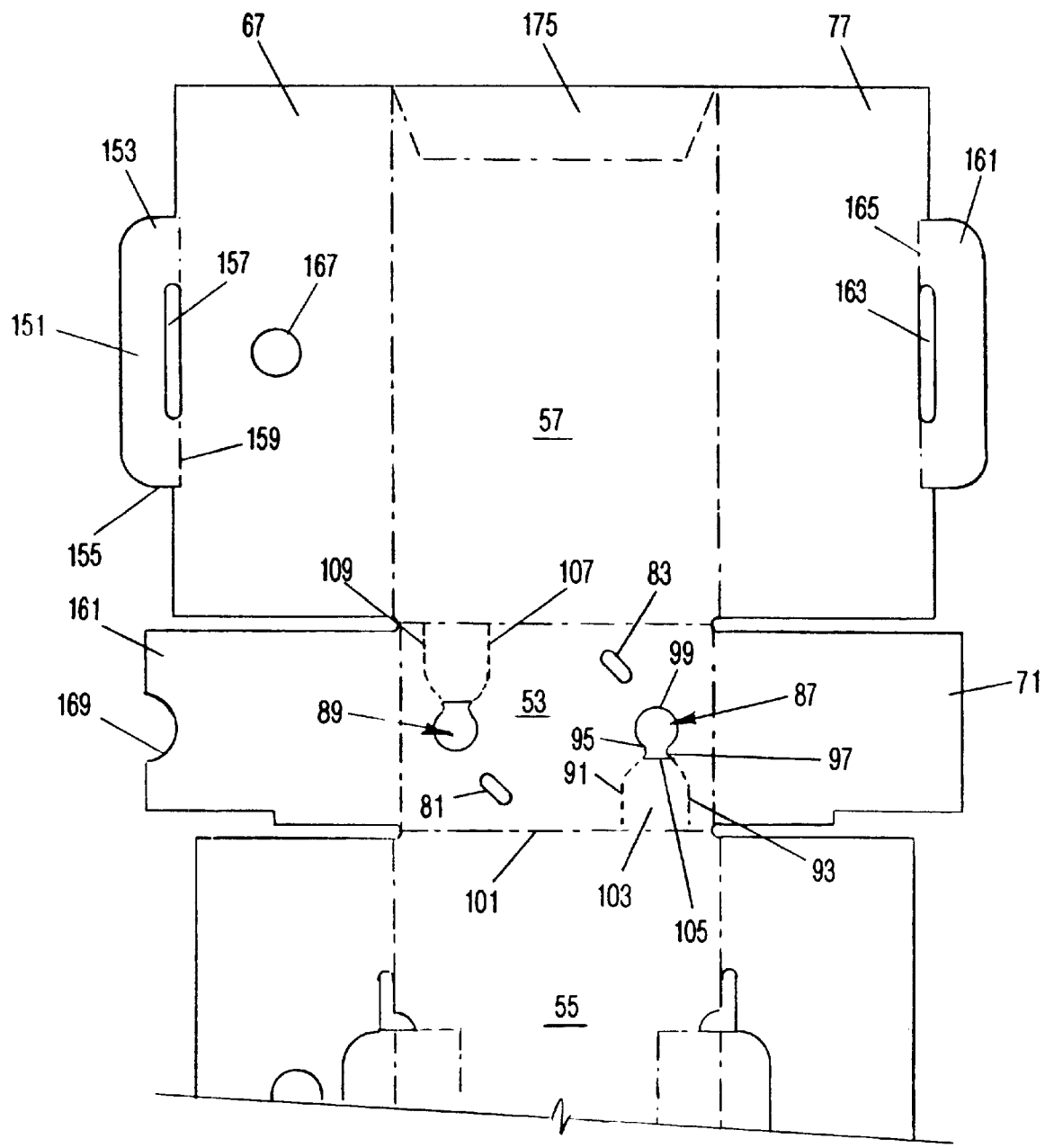
FIGS. 5A and 5B are a plain view of the sheath fluid container of the present invention.
Figure 5B:
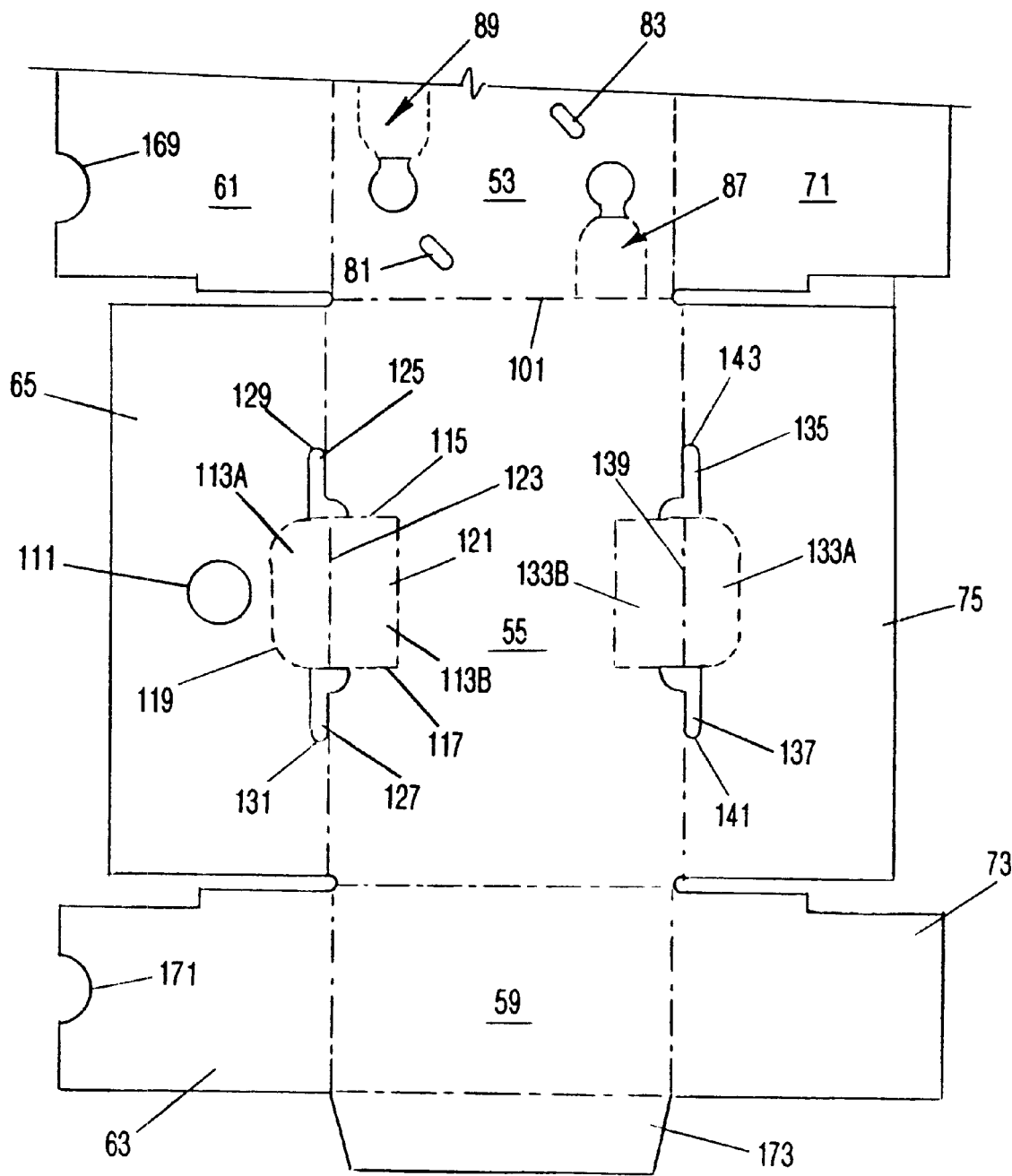
Figure 6:
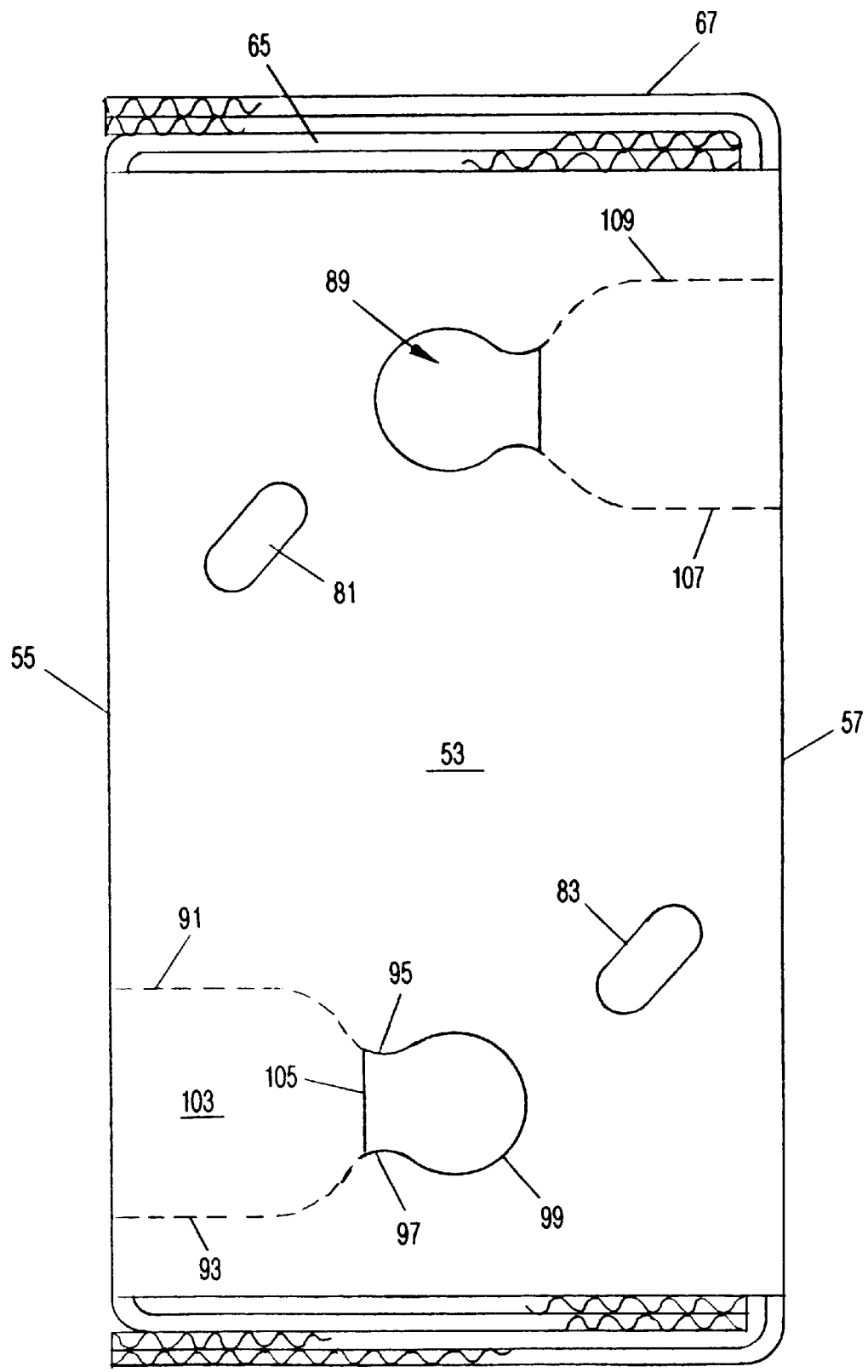
FIG. 6 is a front view of the sheath fluid container of the present invention, in its assembled form, but without the collapsible/expandable sheath fluid reservoirs and the container handle.

Sheath fluid container 11 is, preferably, cut from a single piece of double thickness corrugated cardboard. With reference to FIGS. 5A and 5B, container 11 includes front panel 53, side panels 55 and 57, and back panel 59. The top of container 11 is formed of four portions: top front flap 61, top back flap 63, intermediate top flap 65, and top cover flap 67. Collectively, when assembled these four portions form a top comprising three layers of double thickness corrugated cardboard. Similarly, the bottom of container 11 is formed of four portions: bottom front flap 71, bottom back flap 73, intermediate flap 75, and bottom cover flap 77.

Front panel 53 includes a pair of rectangular slots 81 and 83 for receiving a plastic handle 85 (illustrated in FIG. 1). Each end of handle 85 includes a pair of integrally formed projections (not shown) which can be pushed through slots 81 and 83 during assembly. After insertion the projections engage the inside of panel 53 to thereby secure handle 85 to container 11.

Front panel 53 also includes a pair of valve retainers 87 and 89. Retainer 87 includes an opening defined by two continuous cuts (which are represented by dashed lines 91 and 93 in front panel 53), neck portions 95 and 97 and an essentially circular opening 99. Cuts 91 and 93, together with fold line 101, form tab 103 which folds outwardly from panel 53. Tab 103 includes a valve engagement lip 105. The diameter of opening 99 is slightly larger than the diameter of groove 31 (of valve 25), which it is designed to receive. Retainer 89 is identical in construction and function with retainer 87. Thus, for instance, dashed lines 107 and 109 represent continuous cuts in front panel 53.

Flap 65 includes a circular opening 111. In its flattened condition, panel 55 and flap 65 include a tab having portions 113A and 113B defined by continuous cuts which represent by dotted lines 115,117 and 119. Tab portion 113B hinges outwardly along line 121. Tab portion 113A folds inwardly, up to 90°, relative to tab portion 113B along fold line 123. Finally, flap 65 includes cut outs 125 and 127. When tab 113A is folded inwardly 90°, the opening it creates in flap 65, together with cut outs 125 and 127 form an elongated slot extending from arc 129 to arc 131. See FIG. 5B. As is also evident from FIG. 5B, panel 55 and flap 75 include a second tab, having portions 133A and 133B, which are formed and function in the same way as described with regard to tab portions 113A and 113B. Flap 75 also includes cut outs 135 and 137 which, when tab portion 133A is folded in along fold line 139, form a slot extending from arc 141 to arc 143.

Flap 67 includes a tab 151 having sides 153 and 155 and a slot 157. Tab 151 folds inward relative to flap 67 along fold line 159. The distance between sides 153 and 155 is slightly less than the distance between arcs 129 and 131. The width of slot 157 is slightly larger than the width of tab portion 113A. Flap 77 also includes a tab 161, slot 163 and fold line 165. The dimensions of tab 161 are identical to tab 151.

Flap 67 includes a circular opening 167 (which is of the same diameter as opening 111 in flap 65) and which, when container 11 is assembled aligns with opening 111. Similarly, flaps 61 and 63 include, respectively, arcuate cut outs 169 and 171 which align with opening 111 when container 11 is assembled. Back panel 59 includes a tab 173, which is glued to area 175 of side panel 57. The through opening defined by openings 111 and 167 and cut outs 169 and 171 is designed to receive an electronic device which will store information as to, for instance, what reservoir 13C contains, whether container 11 has been used, and how much sheath fluid remains in reservoir 13C.

Container 11 is assembled by folding along the various fold lines (indicated by dash-dot lines in FIGS. 5A and 5B). Tab 173 is first glued to area 175 of side panel 57. Flaps 71 and 73 are then folded inward, followed by folding over flap 75 and, then, flap 77. Tab 161 is folded inward and inserted in the slot which extends from arc 139 to arc 141. Tab portion 133A is then folded over and inserted into slot 163.

Before the top of container 11 is closed, first clear sheath fluid reservoir 13C and then waste sheath fluid reservoir 13W are inserted. Reservoir 13C is full. Reservoir 13W is essentially empty except for an amount of chlorine bleach or other disinfectant sufficient to sterilize the volume of waste sheath fluid which it will eventually contain. To insert reservoir 13C, tab 103 is bent outward along fold line 101. Thereafter valve 25 is inserted in the partially rectangular opening formed by folding tab 103 outward. The valve 25 is then moved laterally so that groove 31 passes past neck portions 95 and 97 and is received in circular opening 99. Thereafter tab 103 is returned to its original position where valve engagement lip 105 underlies element 33 and holds valve 25 in place. Therefore, reservoir 13W, which has been pleated (i.e. folded back and forth) is laid on top of reservoir 13C, as generally illustrated in FIG. 2, and its valve 25 attached to front panel 53 in the same manner as described above with regard to valve 25 of reservoir 13C.

After insertion of both reservoirs, flaps 61 and 63 are folded down, then flap 65 and, finally, flap 67. Tab 151 is received in the slot defined by, inter alia, arcs 127 and 129. Tab 113A is received in slot 157.

With valve caps 49 in place, the assembled and filled container 11 has a shelf life of approximately two years.

With exterior container 11 dimensions of, approximately, 5"×8"×12", reservoir 13C holds, again approximately, four liters of clean sheath fluid.

In operation, valve caps 49 are removed and connectors 181C and 181W attached to the two valves 25. See FIG. 1. Connector 181 C is coupled to tubing 15C; connector 181W, to tubing 15W. In the process of attachment, plungers 41 are pushed inward to permit the flow of clean fluid from the clear sheath fluid reservoir, through tubing 15C, through the fluidic passages of flow cytometer 17. The opening of valve 25 on the waste sheath fluid reservoir 13W permits waste fluid under pressure from the pump of the flow cytometer to flow through tubing 15W into the waste fluid reservoir. By placing reservoir 13W above reservoir 13C, the flow cytometer pump does not have to work hard to pump the waste sheath fluid into reservoir 13W. As clean sheath fluid volume decreases the waste fluid reservoir increases, keeping the volume in container 11 essentially constant. Once the clean fluid reservoir is essentially empty and, correspondingly, the waste fluid reservoir full, connectors 181 C and 181W are removed, permitting valves 25 to close. Container 11 is then disposed of according to the applicable regulations. This constant volume reservoir system can be effectively utilized with flow cytometers using a pump delivery mode, or those using pressurized sheath delivery, such as that described in U.S. Pat. No. 4,844,610.

Where the drawings and accompanying description have shown and described the preferred embodiment of the present invention, it should be apparent to those skilled in the art that various changes may be made in the form of the invention without affecting its scope. All patents and references described here are incorporated by reference.

What is claimed is:

1. A container for holding both the clean and waste sheath fluid of a flow cytometer, said container comprising:
   a first collapsible reservoir having a first valve therein, said first reservoir containing a volume of clean sheath fluid;
   a second reservoir expandable to a second volume, said second reservoir having a second valve therein; and
   a single housing for both said first and second reservoirs, whereby as said volume of clean sheath fluid of said first reservoir decreases, said second volume of said second reservoir increases with the addition of waste sheath fluid.

2. The container of claim 1, wherein said first reservoir is made of a flexible waterproof material.

3. The container of claim 2, wherein said second reservoir is made of a flexible waterproof material.

4. The container of claim 3, wherein said first and second reservoirs are made from aluminum coated Mylar™.

5. The container of claim 1, wherein said second reservoir contains a volume of disinfectant sufficient to sterilize said waste sheath fluid.

6. The container of claim 1, wherein said housing is disposable.

7. The container of claim 6, wherein said housing is made of cardboard or plastic.

8. The container of claim 1, wherein said container has first and second cutouts and associated first and second tabs for holding said first and second valves.

9. The container of claim 1, wherein said second reservoir is placed above said first reservoir.

10. A method of reducing the combined volumes of two sheath fluid reservoirs, said method including the steps of:
    a. providing a first collapsible reservoir having a first valve therein, said first reservoir containing a volume of clean sheath fluid;
    b. providing a second reservoir expandable to a second volume, said second reservoir having a second valve therein;
    c. providing a single housing for both said first and second housings;
    d. removing clean sheath fluid from said first reservoir, via said first valve;
    e. cycling said removed clean sheath fluid through a flow cytometer; and
    f. filling said second reservoir, via said second valve, with said sheath fluid which has cycled through said flow cytometer.

11. The method of claim 10, wherein said second volume is essentially equal to said first volume.

12. The method of claim 10, wherein as the volume of said clean sheath fluid decreases, the volume of said sheath fluid which has been cycled through said flow cytometer increases, whereby the volume of fluid in first and second reservoirs remains essentially consistent.

* * * * *